United States Patent
Goto

(10) Patent No.: US 11,733,062 B2
(45) Date of Patent: Aug. 22, 2023

(54) MAGNETIC MEASURING APPARATUS

(71) Applicant: Kazuma Goto, Ishikawa (JP)

(72) Inventor: Kazuma Goto, Ishikawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 17/649,230

(22) Filed: Jan. 28, 2022

(65) Prior Publication Data
US 2022/0291018 A1   Sep. 15, 2022

(30) Foreign Application Priority Data
Mar. 10, 2021  (JP) ................ 2021-037995

(51) Int. Cl.
| | | |
|---|---|---|
| G01B 7/14 | (2006.01) | |
| G01B 7/30 | (2006.01) | |
| G01R 33/02 | (2006.01) | |
| G01D 5/12 | (2006.01) | |
| G01D 5/14 | (2006.01) | |
| G01D 5/48 | (2006.01) | |
| G01B 7/00 | (2006.01) | |

(52) U.S. Cl.
CPC .............. *G01D 5/12* (2013.01); *G01D 5/145* (2013.01); *G01D 5/147* (2013.01); *G01D 5/485* (2013.01); *G01B 7/003* (2013.01); *G01B 7/14* (2013.01); *G01B 7/30* (2013.01)

(58) Field of Classification Search
CPC .......... G01D 5/12; G01D 5/145; G01D 5/485; G01D 5/147; A61B 5/062; A61B 5/7217; A61B 5/245; G01B 7/003; G01B 7/14; G01B 7/30
USPC .................. 324/51, 55, 200, 207.11, 207.13
See application file for complete search history.

(56) References Cited

U.S. PATENT DOCUMENTS

| | | | | |
|---|---|---|---|---|
| 2007/0188946 A1* | 8/2007 | Shoji | .................... | G01R 33/093 360/324.12 |
| 2012/0326716 A1* | 12/2012 | Kawase | ............... | G01R 15/148 324/263 |
| 2014/0218018 A1* | 8/2014 | Ivanov | .................... | G01R 33/02 324/252 |
| 2015/0028855 A1* | 1/2015 | Kim | .................... | G01R 33/0052 324/202 |

(Continued)

FOREIGN PATENT DOCUMENTS

JP  2017-217457  12/2017

OTHER PUBLICATIONS

Satoshi Sumiya et al., "Magnetospinography visualizes electrophysiological activity in the cervical spinal cord", Scientific Reports, Received on Jan. 4, 2017, pp. 1-12.

(Continued)

*Primary Examiner* — Raul J Rios Russo
(74) *Attorney, Agent, or Firm* — IPUSA, PLLC

(57) ABSTRACT

A magnetic measuring apparatus includes at least one magnetic sensor, a coil, a driving circuit configured to supply a current to the coil, a conductor electrically connecting the coil and the driving circuit, and a computing device which estimates relative positions of the magnetic sensor and the coil based on a magnetic field generated by the current supplied to the coil and detected by the magnetic sensor. The magnetic sensor has a magnetic detection sensitivity in a particular direction, and the particular direction of the magnetic sensor and a current vector of the current flowing through the conductor are parallel.

9 Claims, 8 Drawing Sheets

(56) References Cited

U.S. PATENT DOCUMENTS

| | | |
|---|---|---|
| 2017/0352457 A1 | 12/2017 | Kubota et al. |
| 2019/0287653 A1 | 9/2019 | Goto |
| 2019/0293689 A1* | 9/2019 | Lerner ................. G01R 15/202 |
| 2020/0293801 A1 | 9/2020 | Goto |
| 2020/0411180 A1 | 12/2020 | Kinoshita et al. |

OTHER PUBLICATIONS

D. Oyama et al., "Real-time Head Localization System for Magnetoencephalography", Journal of Magnetics of Society of Japan, J-STAGE Advanced Publication Dated Sep. 26, 2012, Faculty of Engineering, Iwate University, with partial English Translation.

* cited by examiner

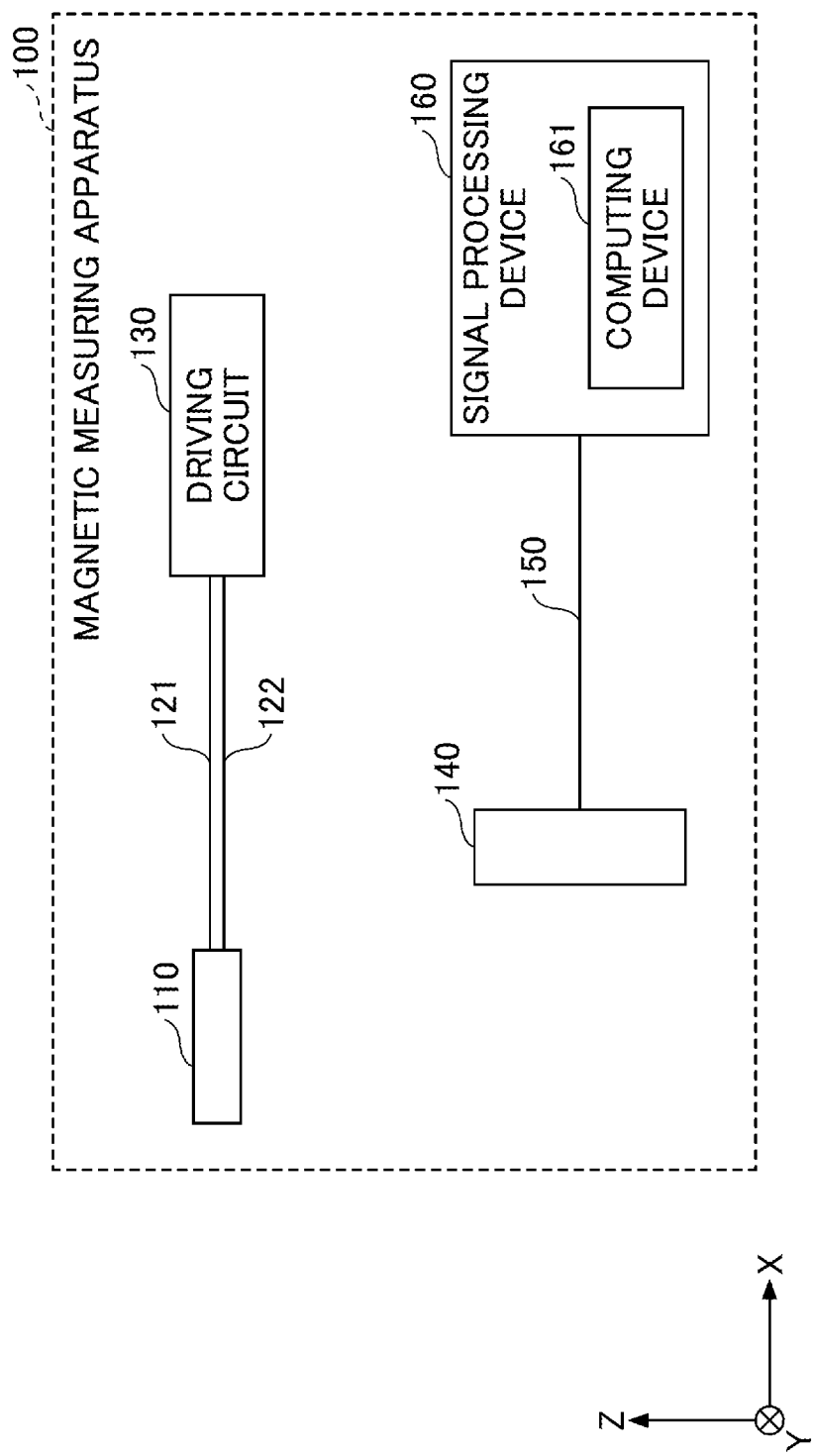

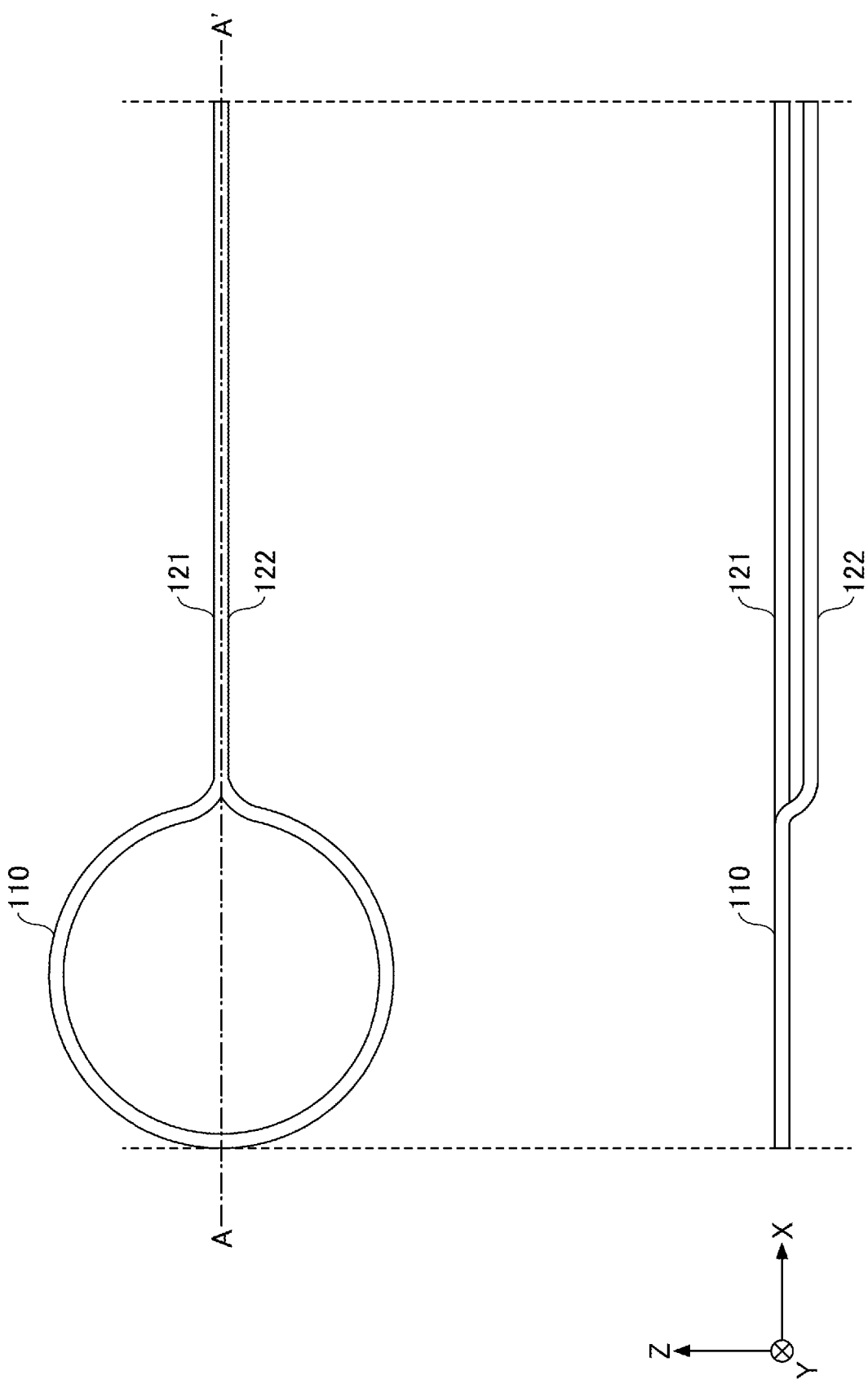

FIG.3

| PARAMETER | VALUE |
|---|---|
| DETECTING DIRECTION OF MAGNETIC SENSOR | X-AXIS DIRECTION/Y-AXIS DIRECTION |
| ARRANGEMENT OF MAGNETIC SENSOR | X-AXIS RANGE: −100 mm TO 100 mm, SPACING: 20 mm<br>Y-AXIS RANGE: −100 mm TO 100 mm, SPACING: 20 mm<br>Z-AXIS POSITION: 0 mm<br>PLURALITY OF MAGNETIC SENSORS ARRANGED IN THE ABOVE RANGE |
| RADIUS OF COIL | 5 mm |
| ARRANGEMENT OF COIL | X-AXIS POSITION: 0 mm/50 mm/100 mm<br>Y-AXIS POSITION: 0 mm/50 mm/100 mm<br>Z-AXIS POSITION: 10 mm/50 mm/100 mm<br>ONE COIL ARRANGED IN THE ABOVE RANGE |
| DIRECTION OF CENTER AXIS OF COIL | Z-AXIS DIRECTION |
| NUMBER OF TURNS OF COIL | 1 |
| DIRECTION OF CURRENT FLOWING THROUGH CONDUCTOR | X-AXIS DIRECTION |
| LENGTH OF CONDUCTOR | 1 m |
| SPACING BETWEEN CONDUCTORS | 30 μm |
| CURRENT FLOWING THROUGH COIL | 100 μA |

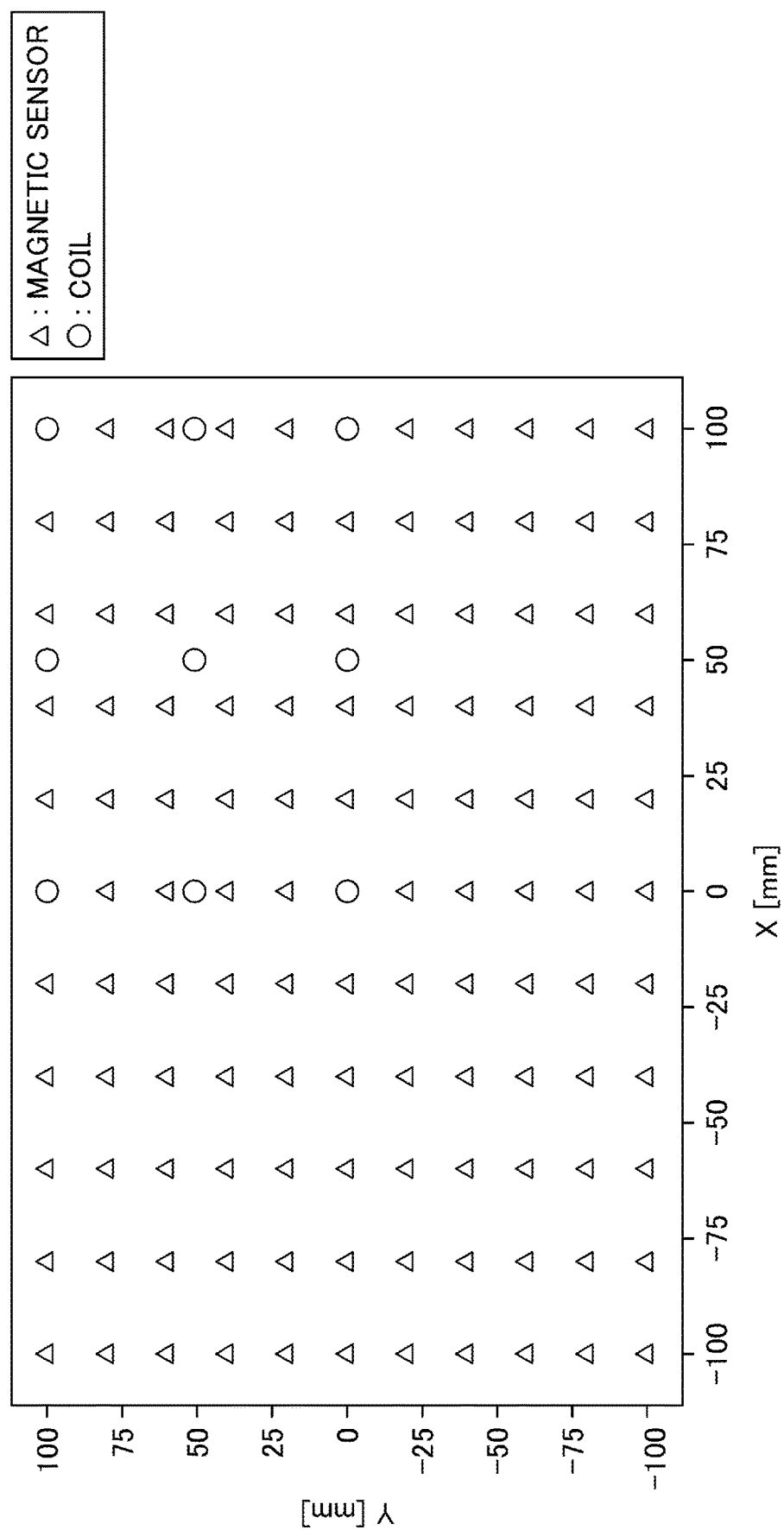

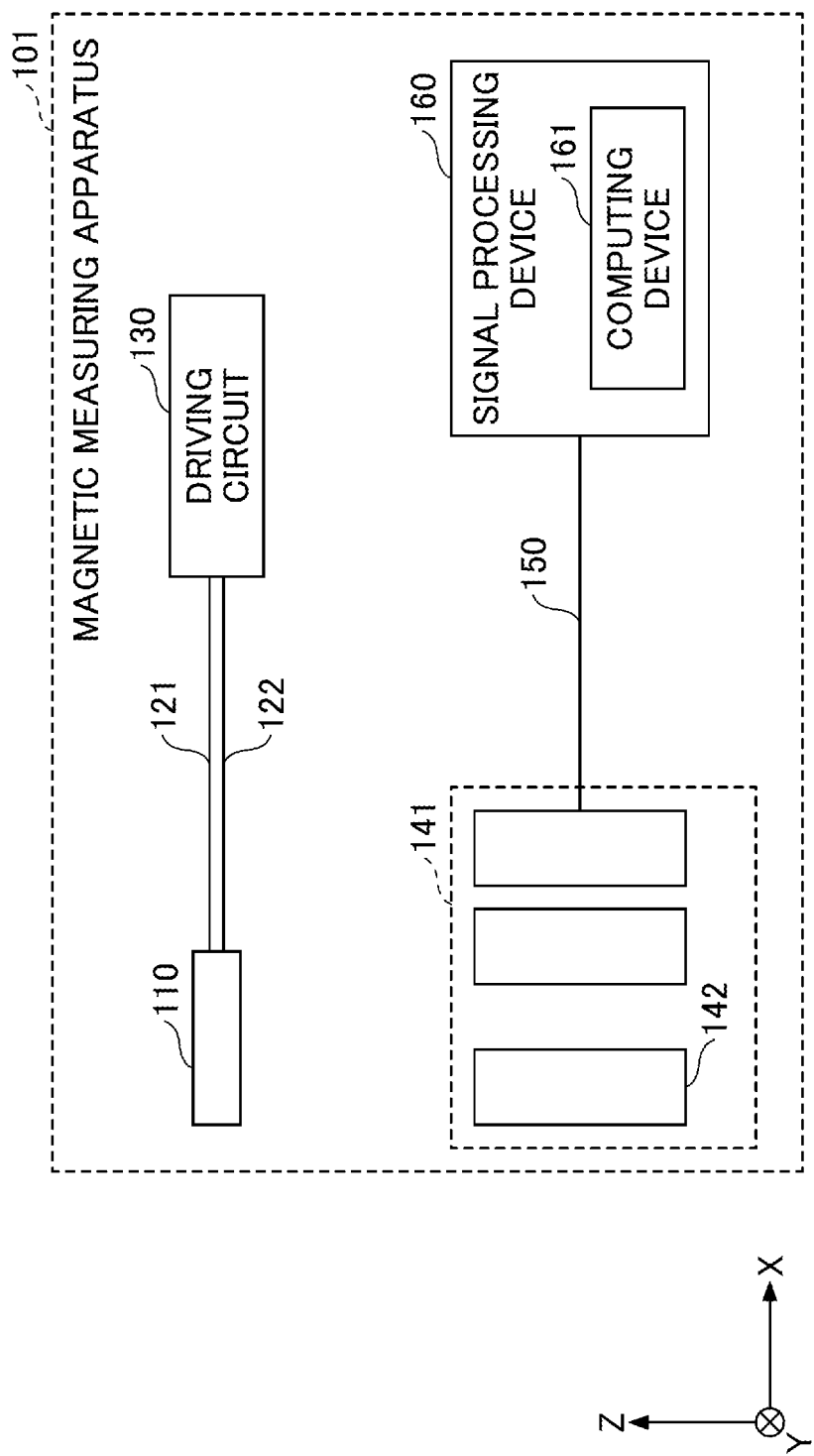

MAGNETIC MEASURING APPARATUS

CROSS-REFERENCE TO RELATED APPLICATIONS

The present application is based upon and claims priority to Japanese Patent Application No. 2021-037995, filed on Mar. 10, 2021, the entire contents of which are incorporated herein by reference.

BACKGROUND OF THE INVENTION

1. Field of the Invention

The present disclosure relates to magnetic measuring apparatuses.

2. Description of the Related Art

Magnetic measuring apparatuses, such as magnetoencephalography systems or the like, measure a weak magnetic field generated by a neural activity using a superconducting quantum interference device (SQUID) sensor array or the like, to determine a position of the main neural activity, based on a relationship between a magnetic field source and a magnetic field distribution. The magnetic measuring apparatuses can measure the magnetic field, but cannot acquire an image of a measuring target, such as the neural activity of a brain, a spinal cord, or the like.

Accordingly, a site (a region, a portion, or the like) of a test subject, where the magnetic field is generated, cannot be determined from the measurement of the magnetic field alone. Hence, by using the magnetic measuring apparatus to measure a weak AC current flowing through a marker coil arranged near a measuring target site of the test subject, it becomes possible to determine a positional relationship between the measuring target site of the test subject and the measured magnetic field.

This type of marker coil is proposed in Japanese Unexamined Patent Application Publication No. 2017-217457, for example. This type of marker coil has a configuration including spiral patterns formed on respective surfaces of a flexible substrate, and two interconnects adjacent to each other on flexible substrate and connected to the spiral patterns. According to this configuration, currents having opposite phases are supplied to the two interconnects supplying the current to the marker coil, to generate the magnetic field only from the marker coil, thereby reducing the generation of the magnetic field due to the current flowing through the interconnects. As a result, the magnetic field generated from the interconnects, as noise other than the magnetic field generated from the marker coil, can be reduced, and a reduction of an error when estimating the position of the marker coil can be expected.

However, depending on the positional relationship between the two insulated interconnects and a magnetic sensor, distances between the magnetic sensor and the two insulated interconnects may differ. In this case, the magnetic sensor may sense the magnetic field generated from the interconnect, and the effect of reducing the error when estimating the position of the marker coil may become limited.

SUMMARY

According to one aspect of the embodiments, a magnetic measuring apparatus includes at least one magnetic sensor; a coil; a driving circuit configured to supply a current to the coil; a conductor electrically connecting the coil and the driving circuit; and a computing device configured to estimate relative positions of the magnetic sensor and the coil based on a magnetic field generated by the current supplied to the coil and detected by the magnetic sensor, wherein the magnetic sensor has a magnetic detection sensitivity in a particular direction, and the particular direction of the magnetic sensor and a current vector of the current flowing through the conductor are parallel.

Other features of the embodiments will be apparent from the following detailed description when read in conjunction with the accompanying drawings.

BRIEF DESCRIPTION OF THE DRAWINGS

FIG. 1 is a block diagram illustrating an example of a configuration of a magnetic measuring apparatus according to a first embodiment;

FIG. 2 is a diagram illustrating an example of a configuration of a coil illustrated in FIG. 1;

FIG. 3 is a diagram illustrating an example of simulation conditions for estimating a position of the coil by the magnetic measuring apparatus and another magnetic measuring apparatus;

FIG. 4 is a diagram illustrating an example of an arrangement of magnetic sensors and coils used in the simulation;

FIG. 8 is a block diagram illustrating an example of the configuration of the magnetoencephalography system according to a second embodiment.

DESCRIPTION OF THE EMBODIMENTS

Figure 5:
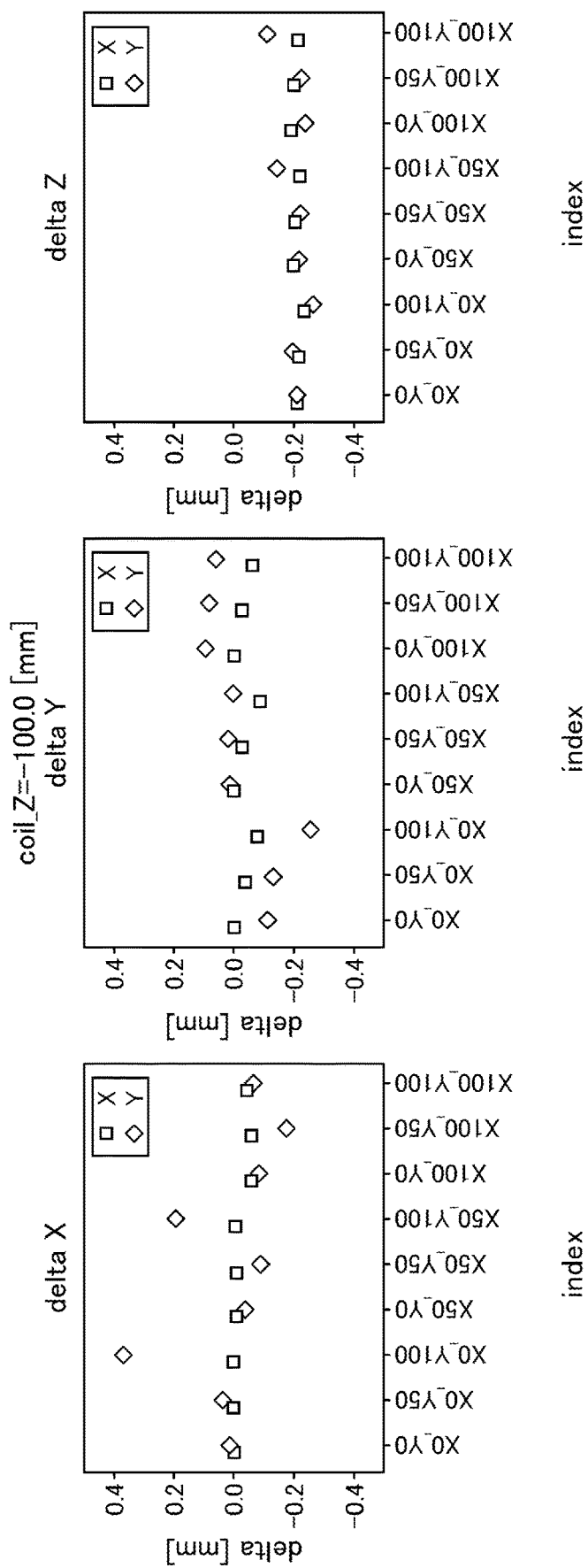
FIG. 5 is a diagram illustrating an example of an estimated error of a coil position (Z=−100 mm) computed by the simulation.

One object according to one aspect of the embodiments is to improve the accuracy of estimating the position of the coil used as a marker (that is, the marker coil) in the magnetic measuring apparatus.

The embodiments will hereinafter be described with reference to the drawings. In drawings, the same constituent elements are designated by the same reference numerals, and a repeated description of the same constituent elements may be omitted.

First Embodiment

FIG. 1 is a block diagram illustrating an example of a configuration of a magnetic measuring apparatus according to a first embodiment. A magnetic measuring apparatus 100 illustrated in FIG. 1 includes a coil 110 used as a marker (hereinafter also referred to a marker coil 110), a driving circuit 130, and a pair of conductors 121 and 122 electrically connecting the coil 110 and the driving circuit 130. The magnetic measuring apparatus 100 also includes a magnetic sensor 140, a signal processing device (or processor, or circuit) 160, and an interconnect 150 electrically connecting the magnetic sensor 140 and the signal processing device 160.

The driving circuit 130 uses the conductors 121 and 122 to supply a current to the coil 110, to generate a magnetic field from the coil 110. The coil 110 may have any shape, as long as the coil 110 is made to generate the magnetic field based on the Biot-Savart law when the current is supplied thereto. The driving circuit 130 is preferably capable of supplying a current having a sinusoidal waveform, in order to detect the magnetic field that is generated when the current is supplied to the coil 110, by distinguishing the magnetic field from external magnetic field noise or the like.

The conductors 121 and 122 are coated with an insulating material having excellent electrical insulating properties, such as polyimide or the like, and are electrically insulated from each other. For example, each of the conductors 121 and 122 is arranged (or disposed) so that a current vector of the current flowing through the conductor becomes parallel to an X-axis direction illustrated in FIG. 1 and FIG. 2. If the direction in which the conductor extends is known, each of the conductors 121 and 122 may be arranged so as to be parallel to a direction other than the X-axis direction. In addition, the conductors 121 and 122 may be arranged with a free orientation at a position sufficiently far from the magnetic sensor 140 such that magnetic sensor 140 cannot detect the magnetic field generated from the conductors 121 and 122.

For example, the conductor 121 is an example of a first conductor along a first current path from driving circuit 130 toward the coil 110. The conductor 122 is an example of a second conductor along a second current path from the coil 110 back toward the driving circuit 130.

The magnetic sensor 140 detects the magnetic field generated from the coil 110 when the current flows through the coil 110, and transmits a signal indicating the detected magnetic field to the signal processing device 160 via the interconnect 150. The magnetic sensor 140 preferably has a magnetic detection sensitivity (or magnetic sensitivity) in only one particular direction. For example, the magnetic sensor 140 includes at least one SQUID sensor. The SQUID sensor requires a cooling mechanism, which is not illustrated in FIG. 1, to maintain the SQUID sensor in a superconducting state.

The magnetic sensor 140 is arranged (or disposed) at a position so as to detect only the X-axis component of the magnetic field. In other words, the magnetic sensor 140 has the magnetic detection sensitivity in the particular direction. Hence, it is possible to reduce the detection of the magnetic field generated due to the current flowing through the conductors 121 and 122. In a case where the conductors 121 and 122 are arranged along an arbitrary direction, the magnetic sensor 140 is arranged so that a detection direction of the magnetic sensor 140 is parallel to the current vector of the current flowing through the conductors 121 and 122.

The signal processing device 160 includes a computing device (or circuit) 161 which performs a data processing on the signal received from the magnetic sensor 140. The signal processing device 160 includes a flux locked loop (FLL) circuit, and an analog-to-digital conversion (ADC) circuit, which are not illustrated in FIG. 1. The signal processing device 160 converts the signal, received from the magnetic sensor 140 through the interconnect 150, into a digital signal.

The computing device 161 assumes the coil 110 as being a magnetic dipole, and solves an inverse problem using an optimization technique based on an amplitude and a phase of a magnetic field waveform detected by the magnetic sensor 140. Thus, the computing device 161 performs a process to derive the position of the coil 110, and can estimate the position of the coil 110 with respect to the position of the magnetic sensor 140, that is, the relative positions of the magnetic sensor 140 and the coil 110.

FIG. 2 is a diagram illustrating an example of a configuration of the coil 110 illustrated in FIG. 1. An upper portion of FIG. 2 illustrates a plan view of coil 110, and a lower portion of FIG. 2 illustrates a cross sectional view of the coil 110. The lower cross sectional view of the coil 110 is along a line A-A' in the upper plan view. The conductors 121 and 122 parallel to the X-axis direction are routed with a spacing in a Z-axis direction.

As described above in conjunction with FIG. 1, the conductors 121 and 122 are coated with the insulating material having the excellent electrically insulating properties, such as polyimide or the like. The coil 110 and the conductors 121 and 122 are famed by a flexible printed circuit (FPC) (or FPC board). By using the FPC, the coil 110 and the conductors 121 and 122 can be famed integrally, thereby facilitating the manufacture of the configuration illustrated in FIG. 2. The spacing (or distance) between the mutually insulated conductors 121 and 122 can easily be reduced to the order of approximately several tens of μm.

FIG. 3 is a diagram illustrating an example of simulation conditions for estimating the position of the coil by the magnetic measuring apparatus 100 according to the first embodiment illustrated in FIG. 1 and by another magnetic measuring apparatus according to a comparative example. The simulation is performed for a case where a plurality of magnetic sensors having the detection direction in the X-axis direction or the Y-axis direction are arranged on an XY-plane in a range illustrated in FIG. 3, including the X-axis range and spacing, the Y-axis range and spacing, and the Z-axis position. The arrangement of the coil and the conductors is varied in 27 levels. For example, the 27 levels are combinations of cases where the arrangement of the coil and the conductors is varied in 9 levels on the X-Y plane, and varied in 3 levels in the Z-axis direction. At least one coil is arranged in a range illustrated in FIG. 3, including the X-axis position, the Y-axis position, and the Z-axis position. For each arrangement of the coil and the conductors, the magnetic field which is generated is computed based on the Biot-Savart law, and the position of the coil is estimated using a computed signal in place of the signal to be measured by the magnetic measuring apparatus.

FIG. 4 is a diagram illustrating an example of the arrangement of the magnetic sensors and the coils used in the simulation. For example, the magnetic sensors are arranged at equal spacings in a range of 200 mm in the Y-axis direction and the X-axis direction, respectively. The number of magnetic sensors, indicated by a triangular symbol "Δ", that are arranged is 11 in each of the Y-axis direction and the X-axis direction in FIG. 1. The number of coils, indicated by a circular symbol "○", that are arranged at equally spacings is 9 in a square area of 100 mm×100 mm at an upper right portion of FIG. 4. In other words, the number of coils that are arranged is 3 in each of the Y-axis direction and the X-axis direction.

Figure 6:
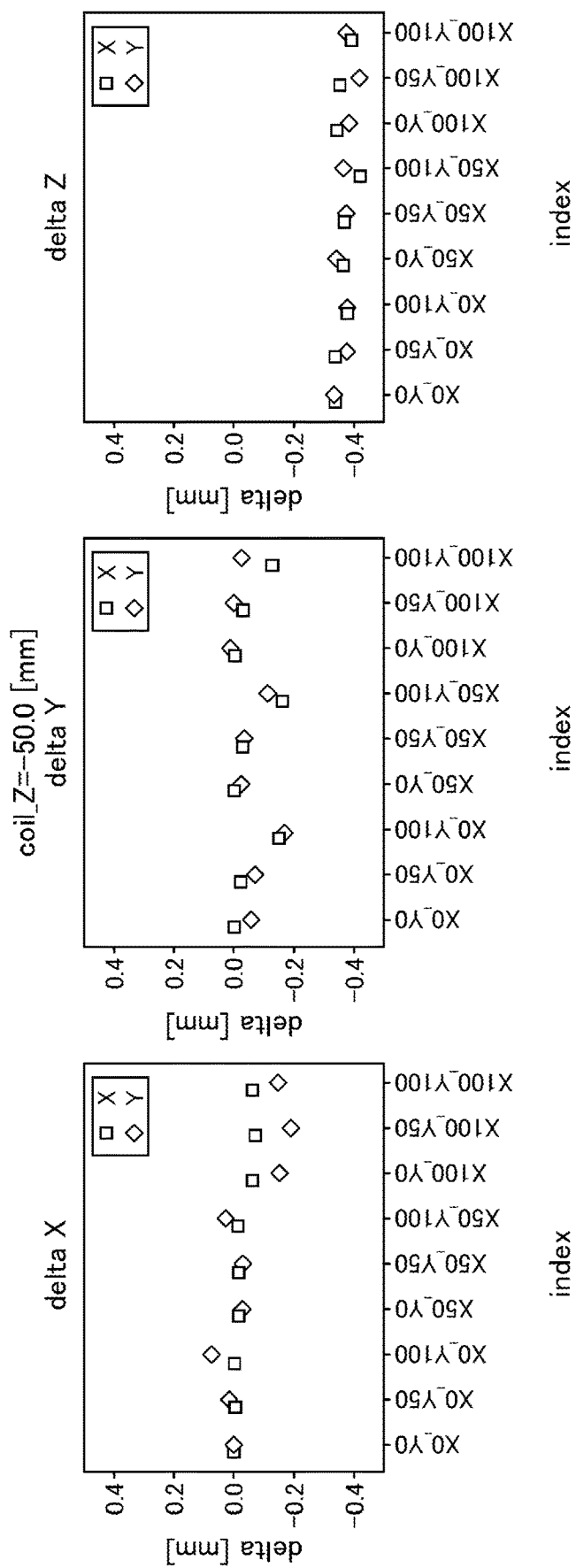
FIG. 6 is a diagram illustrating an example of the estimated error of a coil position (Z=−50 mm) computed by the simulation.
Figure 7:
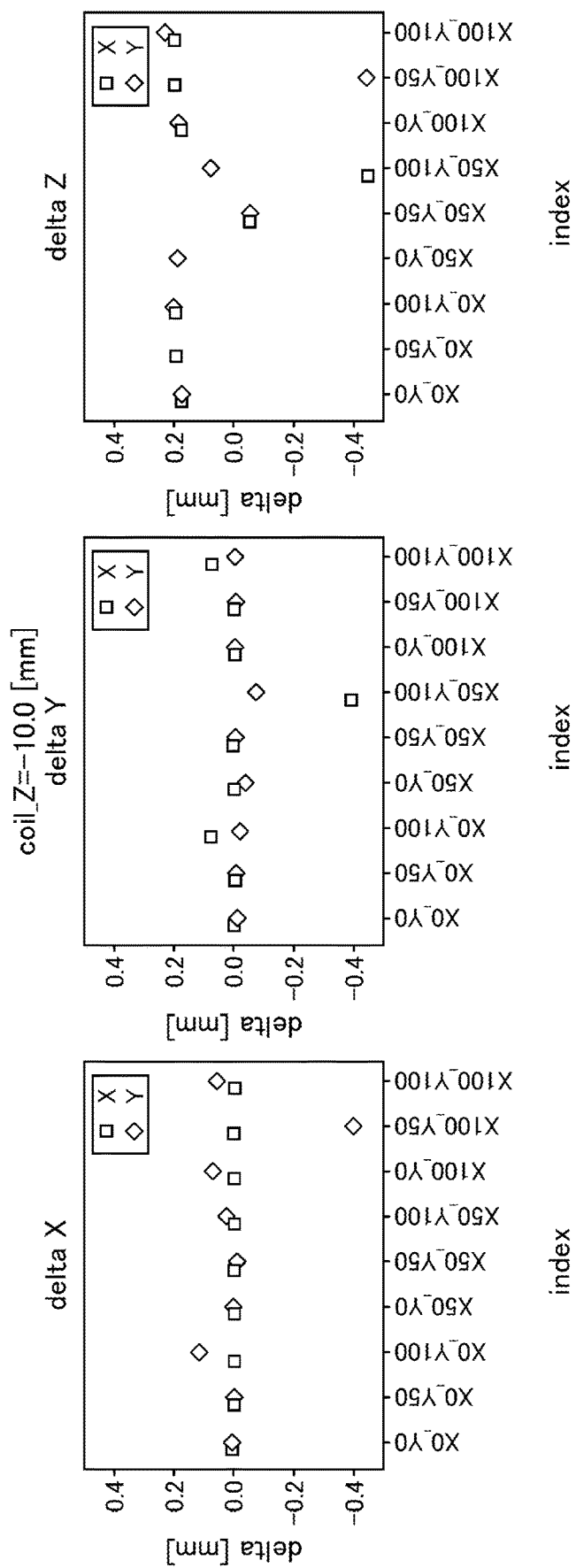
FIG. 7 is a diagram illustrating an example of an estimated error of a coil position (Z=−10 mm) computed by the simulation.

FIG. 5 through FIG. 7 are diagrams illustrating examples of an estimated error of the position of the coil computed by the simulation. FIG. 5 illustrates the simulation results for a case (coil_Z=−100.0 [mm]) where the coil is arranged at a "−100 mm" position along the Z-axis direction in FIG. 1 with respect to the XY-plane. FIG. 6 illustrates the simulation results for a case (coil_Z=−50.0 [mm]) where the coil is arranged at a "−50 mm" position along the Z-axis direction with respect to the XY-plane. FIG. 7 illustrates the simulation results for a case (coil_Z=−10.0 [mm]) where the coil is arranged at a "−10 mm" position along the Z-axis direction with respect to the XY-plane.

The estimated error of the coil position can be computed from the following formulas (1), (2), and (3), where Erx denotes the estimated error in the X-axis direction, Ery denotes the estimated error in the Y-axis direction, Erz denotes the estimated error in the Z-axis direction, Cex denotes the estimated position of the coil in the X-axis direction, Cpx denotes the position of the coil in the X-axis direction, Cey denotes the estimated position of the coil in the Y-axis direction, Cpy denotes the position of the coil in the Y-axis direction, Cez denotes the estimated position of the coil in the Z-axis direction, and Cpz denotes the position of the coil in the Z-axis direction.

$$Erx=Cex-Cpx \quad (1)$$

$$Ery=Cey-Cpy \quad (2)$$

$$Erz=Cez-Cpz \quad (3)$$

In the simulations performed under the conditions of FIG. 3 and FIG. 4, the current vector of the current flowing through the conductor is parallel to the X-axis direction. Accordingly, in FIG. 5 through FIG. 7, the simulation results of the estimated error of the coil position are illustrated by regarding the case where the detection direction of the magnetic sensor is the X-axis direction, for example, as being a case where the measurement is made by the magnetic measuring apparatus 100 illustrated in FIG. 1, and regarding the case where the detection direction of the magnetic sensor is the Y-axis direction, for example, as being a case where the measurement is made by the other magnetic measuring apparatus. In FIG. 5 through FIG. 7, "□ X" indicates the simulation results "□" of the estimated error of the coil position when the detection direction "X" of the magnetic sensor is the X-axis direction for the magnetic measuring apparatus 100 according to the first embodiment, and "◇ Y" indicates the simulation results "◇" of the estimated error of the coil position when the detection direction "Y" of the magnetic sensor is the Y-axis direction for the other magnetic measuring apparatus according to the comparative example.

In each of the graphs illustrated in FIG. 5 through FIG. 7, the abscissa indicates the position of the coil indicated by the circular symbol "○" in FIG. 4, as an "index", and the ordinate indicates the difference (estimated error) between the position of the virtually arranged coil (or virtual coil position) and the estimated position of the coil (or estimated coil position), as "delta". Hence, "delta X" indicates the estimated error of the coil position in the X-axis direction, "delta Y" indicates the estimated error of the coil position in the Y-axis direction, and "delta Z" indicates the estimated error of the coil position in the Z-axis direction. For this reason, the smaller the difference becomes, the more accurate the estimated coil position becomes. For example, X50_Y50 on the abscissa indicates a coil position at X=50 mm and Y=50 mm in FIG. 4. Further, in each of FIG. 5 through FIG. 7, the three graphs from the left to right illustrate the estimated error of the coil position in the X-axis direction, the estimated error of the coil position in the Y-axis direction, and the estimated error of the coil position in the Z-axis direction, respectively.

From the simulation results illustrated in FIG. 5 through FIG. 7, it may be seen that the estimated error of the coil position can be reduced when the detection direction of the magnetic sensor is the X-axis direction (that is, the direction parallel to the conductors 121 and 122 in FIG. 2) as in the first embodiment, compared to when the detection direction of the magnetic sensor is the Y-axis direction as in the comparative example. It may also be seen that the effect of reducing the estimated error of the coil position is enhanced as the coil moves further away from the XY-plane on which the magnetic sensor is arranged.

As described above, in this embodiment, it is possible to reduce the effects of the magnetic field noise generated from other than the coil 110 on the magnetic field measurement of the magnetic measuring apparatus 100, by using the coil 110 having the configuration illustrated in FIG. 2. Hence, the position of the coil 110 can be accurately estimated during the measurement of a biomagnetic field by the magnetic measuring apparatus 100. As a result, it is possible to accurately measure the neural activity of a living body computed based on the measurement of the biomagnetic field by the magnetic measuring apparatus 100.

In addition, the position of the coil 110 can be accurately estimated, even when using the coil 110 and the conductors 121 and 122 that are integrally formed by use of the FPC.

Second Embodiment

FIG. 8 is a block diagram illustrating an example of the configuration of the magnetic measuring apparatus according to a second embodiment. Although the first embodiment described above includes one or more magnetic sensors having the magnetic detection sensitivity in a single direction, the second embodiment which will be described hereinafter includes a plurality of magnetic sensors respectively having the magnetic detection sensitivity in the single direction, and these magnetic sensors are arranged so as to have the magnetic detection sensitivity in various directions.

The magnetic measuring apparatus 101 illustrated in FIG. 8 includes a magnetic sensor array 141 in place of the magnetic sensor 140 of the magnetic measuring apparatus 100 illustrated in FIG. 1. Otherwise, the configuration of the magnetic measuring apparatus 101 is similar to that of the magnetic measuring apparatus 100 illustrated in FIG. 1.

The magnetic sensor array 141 includes a plurality of magnetic sensors 142 respectively having a magnetic detection sensitivity in a single direction. At least one of the magnetic sensors 142 is arranged so that the magnetic detection sensitivity thereof is in the direction (the direction in which the magnetic field is detected) parallel to the conductors 121 and 122 connected to the coil 110.

A known magnetic measuring apparatus includes a plurality of magnetic sensors having magnetic detection sensitivities in the X-axis, Y-axis, and Z-axis directions, respectively, in order to measure the magnetic field caused by neural activity in the living body. This known magnetic measuring apparatus having the magnetic detection sensitivities in the X-axis, Y-axis, and Z-axis direction, respectively, can easily detect signal sources that move in various directions according to the neural activity. Even in this known magnetic measuring apparatus, the conductors 121 and 122 may be arranged parallel to the direction of the magnetic detection sensitivity of at least one of the magnetic sensors, to reduce the estimated error in the position of the coil 110, as illustrated in FIG. 5 through FIG. 7.

The computing device 161 illustrated in FIG. 8 selects only the signal from the magnetic sensor 142 arranged parallel to the conductors 121 and 122, from among the signals processed by the signal processing device 160. After selecting the signal, the computing device 161 can estimate the coil position by performing a process similar to that performed in the first embodiment described above.

As described above, in this embodiment, similar to the first embodiment, it is possible to reduce the effects of the magnetic field noise generated from other than the coil 110 on the magnetic field measurement of the magnetic measuring apparatus 101, by using the coil 110 having the configuration illustrated in FIG. 2. Hence, the position of the coil 110 can be accurately estimated during the measurement of the biomagnetic field by the magnetic measuring apparatus 101. As a result, it is possible to accurately measure the neural activity of the living body computed based on the measurement of the biomagnetic field by the magnetic measuring apparatus 101.

According to each of the embodiments described above, it is possible to improve the accuracy of estimating the position of the coil used as a marker (that is, the marker coil) in the magnetic measuring apparatus.

Although the embodiments are numbered with, for example, "first," or "second," the ordinal numbers do not imply priorities of the embodiments.

Numerous additional modifications and variations are possible in light of the above teachings. It is therefore to be understood that, within the scope of the appended claims, the disclosure of this patent specification may be practiced otherwise than as specifically described herein.

As can be appreciated by those skilled in the computer arts, the present invention may be implemented as convenient using a conventional general-purpose digital computer programmed according to the teachings of the present specification. Appropriate software coding can readily be prepared by skilled programmers based on the teachings of the present disclosure, as will be apparent to those skilled in the software arts. The present invention may also be implemented by the preparation of application specific integrated circuits (ASICs) or by interconnecting an appropriate network of conventional component circuits, as will be readily apparent to those skilled in the relevant art.

Each of the functions of the described embodiments may be implemented by one or more processing circuits. A processing circuit may encompass a programmed processor. A processing circuit may also encompass devices such as an application specific integrated circuit (ASIC) and conventional circuit components arranged to perform the recited functions.

The processing circuitry is implemented as at least a portion of a microprocessor. The processing circuitry may be implemented using one or more circuits, one or more microprocessors, microcontrollers, ASICs, dedicated hardware, digital signal processors (DSPs), microcomputers, central central processing units (CPUs), field programmable gate arrays (FPGAs), programmable logic devices, state machines, super computers, or any combination thereof. Also, the processing circuitry may encompass one or more software modules executable within one or more processing circuits. The processing circuitry may further encompass a memory configured to store instructions and/or code that causes the processing circuitry to execute functions.

If embodied in software, each block may represent a module, segment, or portion of code that comprises program instructions to implement the specified logical function(s). The program instructions may be embodied in the foam of source code that comprises human-readable statements written in a programming language or machine code that comprises numerical instructions recognizable by a suitable execution system such as a processor in a computer system or other system. The machine code may be converted from the source code, or the like. If embodied in hardware, each block may represent a circuit or a number of interconnected circuits to implement the specified logical function(s).

What is claimed is:

1. A magnetic measuring apparatus comprising:
   a magnetic sensor;
   a coil;
   a driving circuit configured to supply a current to the coil;
   a conductor electrically connecting the coil and the driving circuit; and
   a processor configured to perform a process including
      estimating relative positions of the magnetic sensor and the coil based on a magnetic field generated by the current supplied to the coil and detected by the magnetic sensor, wherein
   the magnetic sensor has a magnetic detection sensitivity in a particular direction, and
   the particular direction and a current vector of the current flowing through the conductor are parallel.

2. The magnetic measuring apparatus as claimed in claim 1, further comprising:
   a plurality of magnetic sensors including the magnetic sensor,
   wherein the processor performs a process including
      estimating the relative position of the coil with respect to one of the plurality of magnetic sensors having a detection direction in which the magnetic field is detected, parallel to the current vector of the current flowing through the conductor.

3. The magnetic measuring apparatus as claimed in claim 2, wherein
   the conductor includes a first conductor along a first current path from the driving circuit toward the coil, and a second conductor along a second current path from the coil back toward the driving circuit, and
   the first conductor and the second conductor are electrically insulated from each other, and arranged parallel to each other.

4. The magnetic measuring apparatus as claimed in claim 1, wherein
   the conductor includes a first conductor along a first current path from the driving circuit toward the coil, and a second conductor along a second current path from the coil back toward the driving circuit, and
   the first conductor and the second conductor are electrically insulated from each other, and arranged parallel to each other.

5. The magnetic measuring apparatus as claimed in claim 4, wherein the coil, the first conductor, and the second conductor are integrally formed on a flexible printed circuit.

6. The magnetic measuring apparatus as claimed in claim 3, further comprising:
   a magnetic sensor array including the plurality of magnetic sensors respectively having a magnetic detection sensitivity in a single direction,
   wherein at least one of the plurality of magnetic sensors is arranged so that the magnetic detection sensitivity thereof is in a direction parallel to the first conductor and the second conductor.

7. The magnetic measuring apparatus as claimed in claim 1, further comprising:
   an interconnect electrically connecting the magnetic sensor and the processor,
   wherein the processor performs the process further including
      performing a data processing on a signal received from the magnetic sensor through the interconnect, and converting the signal received from the magnetic sensor through the interconnect into a digital signal.

8. The magnetic measuring apparatus as claimed in claim 1, wherein the processor performs the process by assuming the coil as being a magnetic dipole, and solving an inverse problem using an optimization technique based on an amplitude and a phase of a magnetic field waveform detected by the magnetic sensor, to thereby derive a. position of the coil.

9. The magnetic measuring apparatus as claimed in claim 1, wherein the magnetic sensor is a superconducting quantum interference device sensor.

* * * * *